United States Patent [19]

Grundmann et al.

[11] Patent Number: 5,213,792

[45] Date of Patent: * May 25, 1993

[54] STORAGE-STABLE PEARLESCENT HAIR-CONDITIONING COMPOSITIONS

[75] Inventors: Karin Grundmann, Edewecht-Friedrichsfehn; Günther Lang, Reinheim; Paul Gross, Darmstadt, all of Fed. Rep. of Germany

[73] Assignee: Wella Aktiengesellschaft, Darmstadt, Fed. Rep. of Germany

[ * ] Notice: The portion of the term of this patent subsequent to Oct. 11, 2005 has been disclaimed.

[21] Appl. No.: 881,606

[22] Filed: May 12, 1992

Related U.S. Application Data

[63] Continuation-in-part of Ser. No. 536,600, Jun. 27, 1990, abandoned.

[30] Foreign Application Priority Data

Aug. 11, 1989 [DE] Fed. Rep. of Germany ....... 3837860

[51] Int. Cl.$^5$ .................. A61K 7/075; A61K 7/08
[52] U.S. Cl. .................... 424/70; 252/547; 252/DIG. 13; 514/938; 514/943
[58] Field of Search ................... 424/70, 71

[56] References Cited

U.S. PATENT DOCUMENTS

| | | | |
|---|---|---|---|
| 4,438,096 | 3/1984 | Preston | 424/70 |
| 4,777,039 | 10/1988 | Lang et al. | 424/70 |
| 5,019,376 | 5/1991 | Nick | 424/70 |

FOREIGN PATENT DOCUMENTS 62-13841 6/1987 Japan .

*Primary Examiner*—Thurman K. Page
*Assistant Examiner*—Raj Bawa
*Attorney, Agent, or Firm*—Michael J. Striker

[57] ABSTRACT

Storage-stable, pearlescent hair conditioning composition consisting of 0.2 to 10 percent by weight glycerin monolauric acid ester, 0.2 to 10 percent by weight of a straight-chain fatty alcohol with 10 to 18 carbon atoms or a mixture of the fatty alcohols, 0.050 to 5 percent by weight of a quaternary compound selected from the group consisting of compounds having the general formula (I):

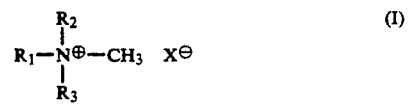

and compounds having the general formula (II):

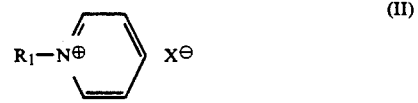

wherein $R_1$ is selected from the group consisting of alkyl radicals having 12 to 22 carbon atoms, cocamidoethyl, cocamidopropyl and $R'-Y-$, and $R'$ is selected from the group consisting of alkyl radicals having 12 to 22 carbon atoms, and Y is $-O-CO-CH_2-$ or $-CO-O-CH_2-CH_2-$; and wherein $R_2$ is $CH_3$, $CH_2CH_2OH$ or $CH_2CH_3$, and wherein $R_3$ is $CH_3$, $CH_2CH_2OH$, benzyl or acetamidyl, and wherein X is Cl, Br, $CH_3SO_4$, $\frac{1}{2}SO_4$, dihydrogen phosphate, acetate or acetate; 70 to 99.595 water; and 0 to 5 percent by weight of a conventional cosmetic additive.

8 Claims, No Drawings

STORAGE-STABLE PEARLESCENT HAIR-CONDITIONING COMPOSITIONS

This application is a continuation-in-part of application Ser. No. 536,600, filed Jun. 27, 1990, now abandoned.

BACKGROUND OF THE INVENTION

The present invention relates to a storage-stable, pearlescent hair conditioning composition based on glycerin monolauric acid ester, fatty alcohols and certain quaternary compounds.

Pearlescent hair conditioning compositions based on fatty alcohols and certain quaternary compounds are already known from U.S. Pat. No. 4,777,039 issued to the present applicants(Equivalent to German Published Patent Application 3 440 935). However, these compositions contain coconut fatty acid monoethanol amide which can form carcinogenic nitrosamines under unfavorable conditions, as has been shown by recent studies.

Hair conditioning compositions which contain (i) a glycerin fatty acid ester (preferably a mixture of glycerin tristearate), (ii) a fatty alcohol, (iii) certain quaternary ammonium salts, and (iv) a polyoxyalkylated ricinoleic fatty acid ester, are likewise known from JP-OS 62 138 412. The compositions described in the latter have satisfactory characteristics with respect to hair conditioning and in technical respects relating to application, but they have no stable pearlescence.

SUMMARY OF THE INVENTION

It is an object of the present invention to provide a pearlescent, cationic hair conditioning composition which contains no fatty acid ester ethanol amides, is unobjectionable in physiological and dermatological aspects and possess a good storage stability, i.e. one in which no phase separation occurs under normal storage conditions for such compositions, in particular at 20° to 40° C. during a storage of some months, especially 3 to 6 months.

It has now been found that this problem is solved according to the invention in an outstanding manner by a hair conditioning composition containing a glycerin monolauric acid ester, certain quaternary compounds, $C_{10}$ to $C_{18}$ fatty alcohols and certain cosmetic ingredients in certain definite proportions.

According to the invention the storage-stable, pearlescent hair conditioning composition consists of:
(A) 0.2 to 10 percent by weight glycerin monolauric acid ester,
(B) 0.2 to 10 percent by weight of a straight-chain fatty alcohol with 10 to 18 carbon atoms or a mixture of the fatty alcohols,
(C) 0.050 to 5 percent by weight of a quaternary compound selected from the group consisting of compounds having the general formula (I):

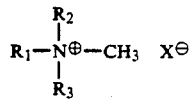

and compounds having the general formula (II):

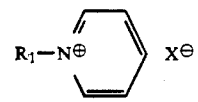

wherein $R_1$ is selected from the group consisting of alkyl radicals having 12 to 22 carbon atoms, cocamidoethyl, cocamidopropyl and $R'$—$Y$—,
and $R'$ is selected from the group consisting of alkyl radicals having 12 to 22 carbon atoms, and
$Y$ is selected from the group consisting of —O—CO—$CH_2$— and —CO—O—$CH_2$—$CH_2$—; and
wherein $R_2$ is selected from the group consisting of $CH_3$, $CH_2CH_2OH$ and $CH_2CH_3$, and
wherein $R_3$ is selected from the group consisting of $CH_3$, $CH_2CH_2OH$, benzyl and acetamidyl, and
wherein X is selected from the group consisting of Cl, Br, $CH_3SO_4$, ½ $SO_4$, dihydrogen phosphate, lactate and acetate; and
(D) 70 to 99.595 water; and
(E) 0 to 5 percent by weight of an additive selected from the group consisting of cosmetic dyestuffs, perfume oils, preservatives, vitamins, antioxidants, thickeners, cosmetic oils, hair care materials, cationic polymers and antidandruff ingredients;
wherein the additive is not present in a greater percentage by weight than the sum of the percentages by weight of the glycerin monolauric acid ester, the fatty alcohol and the quaternary compound, and
wherein the percent by weight of the glycerin monolauric acid divided by the percent by weight of the fatty alcohol is from 0.3 to 5, and
wherein the percent by weight of the quaternary compound divided by a sum of the percent by weight of the glycerin monolauric acid and the fatty alcohol is from 0.01 to 0.4.

The hair conditioning composition, according to the invention, has a very good combability improving action, a uniform viscosity, a stable pearlescent appearance and a good storage life.

Only those commercial products having a degree of purity of at least 90 % can be used as glycerin monolauric acid ester of component (A).

It is particularly advantageous if the glycerin monolauric acid ester of component (A) is contained in the composition, according to the invention, in a quantity of 0.5 to 4 percent by weight.

The particularly preferred quantity of fatty alcohol of component (B) is 0.8 to 5 percent by weight. All straight-chain fatty alcohols with 10 to 18 carbon atoms, e.g. lauryl alcohol, tetradecanol, cetyl alcohol and stearyl alcohol, can be taken into consideration as fatty alcohols. Further, component (B) can comprise a mixture of these fatty alcohols, e.g. a 1:1 mixture of cetyl alcohol and stearyl alcohol (commercial product LANETTER ® 0 from the Henkel Company, Dusseldorf).

Suitable quaternary compounds of component (C) are chiefly quaternary ammonium compounds, e.g. lauryl trimethylammonium chloride, tetradecyltrimethylammonium chloride, cetyltrimethylammonium chloride, stearyl trimethylammonium chloride, cetyldimethylhydroxyethyl ammonium dihydrophophate, cetyldimethylbenzylammonium chloride; further, pyridinium salts, e.g. cetylpyridinium chloride and other quaternary compounds such as e.g. lauric acid choline ester chloride, betaine cetylester chloride and coconut fatty acid amidopropyldimethylacetamidyl ammonium chloride. The quaternary compounds of component (C) are preferably contained in the composition, according to the invention, in a quantity of 0.1 to 1.5 percent by weight.

The main quantity of the composition, according to the invention, consists of water, wherein the water content is preferably 90 to 97 percent by weight. Although tap water can be used if it contains a relatively low quantity of ions, it is advantageous to use deionized water.

The hair conditioning composition described here can further contain all those cosmetic additives usually used in hair conditioning compositions, particularly dyestuffs, perfume oils, vitamins, preservatives, antioxidants and antidandruff ingredients. The aforementioned ingredients or additives can be contained in a quantity of approximately 0.1 to 1 percent by weight. Other conventional ingredients are e.g. cosmetic oils such as avocado oil, or hair care materials such as lanolin, cholesterin and pantothenic acid, wherein these ingredients can be contained in a quantity of approximately 0.1 to 5 percent by weight. Among the references describing cosmetic oils in more detail are Ph. Alexander 'Conventional Oils of Vegetable and Animal origin', SPC, pp. 381-384 (1985) and Ph. Alexander 'Cosmetic Oils and Their Applications', Part 2, SPC, pp. 509 to 517 (1985).

The composition can also contain cationic polymers as well as thickeners, e.g. starch, cellulose derivatives or highly dispersed silicic acid (e.g. Aerosil® 300 from Degussa Copmany, Hanau, Federal Republic of Germany) in a quantity of approximately 0.1 to 2 percent by weight. Cationic polymers are described in greater detail in the article 'Update on Hair Conditioner Ingredients', by B. Idson and W. Lee in Cosmetics and Toiletries 98. pp. 41 to 46(1983).

The hair conditioning composition, according to the invention, can also be in the form of an aerosol preparation and, in this case, contains approximately 1 to 10 percent by weight of a propellant as additional conventional ingredient. Chlorofluoroalkanes such as e.g. $CCl_3F$, $CCl_2F_2$, $C_2Cl_3F_3$, $CCl_2F$—$CCl_2F$, $CHCl_2F$, $CHClF_2$ and $CClF_2$—$CClF_2$, slightly volatile hydrocarbons such as n-butane, i-butane, i-butane and n-propane or dimethylether, $CO_2$, $N_2O$, $N_2$, $CH_2Cl_2$ and $CCl_3$—$CH_3$ as well as mixtures of the aforementioned materials can be used as propellant.

The production of the composition, according to the invention, is conventionally carried out according to the production processes known for cosmetic emulsions in that e.g. the hydrophobic constituents (components (A) and (B) and other hydrophobic ingredients which may be contained) are first melted at 70° to 90° C. The hydrophylic constituents (component (C) as well as hydrophylic ingredients) are dissolved in water; the aqueous solution thus obtained is heated to 70 to 90° C and emulsified in the melt of hydrophobic constituents accompanied by stirring. Finally, the resulting emulsion is cooled.

The following examples will explain the subject matter of the invention in more detail without limiting the subject matter to these examples.

EXAMPLES

Examples 1 to 5:
Influence of the glycerin fatty acid ester on the forming of pearlescence

| Example (quantities given in grams) | | 1 | 2 | 3 | 4 | 5 |
|---|---|---|---|---|---|---|
| (A) | glycerin mono-lauric acid ester | — | — | 1.24 | 2.48 | 2.14 |
| | glycerin mono-stearic acid ester | — | 2.14 | 1.24 | — | — |
| | glycerin mono-distearic acid ester | 5.00 | — | — | — | — |
| (B) | stearyl alcohol | 3.36 | 1.43 | 2.07 | 2.07 | 1.43 |
| (C) | stearyl-trimethyl-ammonium chloride | 2.62 | 1.43 | 0.45 | 0.45 | 1.43 |
| | dyestuff | 1.00 | 1.00 | 1.00 | 1.00 | 1.00 |
| | perfume oil | 0.50 | 0.50 | 0.50 | 0.50 | 0.50 |
| | water (deionized) | 87.52 | 93.50 | 93.50 | 93.50 | 93.50 |
| | | 100.00 | 100.00 | 100.00 | 100.00 | 100.00 |
| (A):(B) = | | ./. | ./. | 0.60 | 1.20 | 1.50 |
| (C):(A) + (B) = | | ./. | ./. | 0.14 | 0.10 | 0.40 |
| Pearlescence | | − | − | + | + | + |

The hydrophobic components are melted at 80 degrees Celsius and emulsified with the aqueous solution of the water-soluble components accompanied by stirring, the aqueous solution being heated to 80 degrees Celsius. After cooling, only cloudy emulsions are obtained in the compositions according to the invention (Examples 3 to 5), have a pearlescent effect. Examples 1 to 5 accordingly prove unequivocally hat a pearlescent hair conditioning composition is obtained only with the use of glycerin monolauric acid ester, but not with the use of other glycerin fatty acid esters.

Examples 6 to 10:
Influence of the ratio of weight of (A) to (B) and (C) to (A) + (B) on the storage stability of the hair conditioning composition

| Example (quantities qiven in grams) | | 6 | 7 | 8 | 9 | 10 |
|---|---|---|---|---|---|---|
| (A) | glycerin mono-lauric acid ester | 1.33 | 7.11 | 3.33 | 6.60 | 1.98 |
| (B) | stearyl alcohol | 6.67 | 0.89 | 1.67 | 3.30 | 2.37 |
| (C) | stearyl-trimethyl-ammonium chloride | 2.00 | 2.00 | 5.00 | 0.08 | 0.65 |
| | perfume oil | 0.50 | 0.50 | 0.50 | 0.50 | 0.50 |
| | water (deionized) | 89.50 | 89.50 | 89.50 | 89.52 | 94.50 |
| | | 100.00 | 100.00 | 100.00 | 100.00 | 100.00 |
| (A):(B) = | | 0.20 | 7.99 | 1.99 | 2.00 | 0.84 |
| (C):(A) + (B) = | | 0.25 | 0.25 | 1.00 | 0.008 | 0.15 |
| Pearlescence | | ○ | ○ | − | + | + |
| storage stability (3 months at 20° C.) | | un-stable, separation | un-stable, separation | ./. | un-stable, separation | stable, no separation |

+ = pearlescence
○ = slight pearlescence
− = no pearlescence

As the preceding examples show, a storage-stable pearlescent composition, that is, one that does not separate during storage, is only obtained when the ratio of weight of (A) to (B) and (C) to (A)+(B) lies within the range according to the invention, as in Example 10.

Examples 11 to 19:
Storage-stable pearlescent hair conditioning composition Examples 11 to 19 show the use of various quaternary compounds and various fatty alcohols, wherein the quantities of components (A), (B) and (C) used likewise vary.

The following hair conditioning compositions are produced in the manner described in Examples 1 to 5. These hair conditioning compositions also have a stable pearlescence after a longer period of storage, wherein the composition according to Example 12 also has a stable pearlescence after months of storage at 40° C.

| Example (quantities given in grams) | | 11 | 12 |
|---|---|---|---|
| (A) | glycerin monolauric acid ester | 2.37 | 2.37 |
| (B) | stearyl alcohol | — | 1.98 |
| (B) | cetylstearyl alcohol | 1.98 | — |
| (C) | stearyltrimethylammonium chloride | 0.65 | 0.65 |
| | perfume oil | 0.50 | 0.50 |
| | water (deionized) | 94.50 | 94.50 |
| | | 100.00 | 100.00 |
| (A):(B) = | | 1.20 | 1.20 |
| (C):[(A) + (B)] = | | 0.15 | 0.15 |

| Example (quantities given in grams) | | 13 | 14 | 15 |
|---|---|---|---|---|
| (A) | glycerin monolauric acid ester | 2.37 | 2.37 | 2.37 |
| (B) | stearyl alcohol | 1.98 | 1.98 | 1.98 |
| (C) | cetyldimethylbenzylammonium chloride | 0.65 | — | — |
| (C) | lauryltrimethylammonium chloride | — | 0.65 | — |
| (C) | $C_{20}$-$C_{22}$-alkyltrimethyl-ammonium chloride | — | — | 0.65 |
| | dyestuff | 1.00 | 1.00 | 1.00 |
| | water (deionized) | 93.50 | 93.50 | 93.50 |
| | | 100.00 | 100.00 | 100.00 |
| (A):(B) | | 1.20 | 1.20 | 1.20 |
| (C):[(A) + (B)] | | 0.15 | 0.15 | 0.15 |

| Example (quantities given in grams) | | 16 | 17 | 18 |
|---|---|---|---|---|
| (A) | glycerin monolauric acid ester | 1.98 | 2.48 | 6.60 |
| (B) | stearyl alcohol | 2.37 | 2.07 | 3.30 |
| (C) | stearyltrimethylammonium chloride | 0.65 | 0.45 | 0.10 |
| | dyestuff | 1.00 | 1.00 | 1.00 |
| | perfume oil | 0.50 | 0.50 | 0.50 |
| | water (deionized) | 93.50 | 93.50 | 88.50 |
| | | 100.00 | 100.00 | 100.00 |
| (A):(B) = | | 0.84 | 1.20 | 2.00 |
| (C):[(A) + (B)] = | | 0.15 | 0.10 | 0.01 |

20 g of the preceding hair conditioning composition were distributed in washed, towel-dried hair and rinsed out with lukewarm water after acting for 3 to 5 minutes. The hair treated in this manner has good combability and an outstanding hold.

Example 19:
Pearlescent hair conditioning composition (hair treatment with body effect)

| (A) | glycerin monolauric acid ester | 1.98 g |
|---|---|---|
| (B) | stearyl alcohol | 2.37 g |
| (C) | stearyltrimethylammonium chloride | 0.65 g |
| | highly dispersed silicic acid (Aerosil ® 300 of the Degussa company) | 0.50 g |
| | perfume oil | 0.50 g |
| | water (deionized) | 94.00 g |

-continued
Example 19:
Pearlescent hair conditioning composition (hair treatment with body effect)

| | | 100.00 g |
|---|---|---|
| (A):(B) = | | 0.84 g |
| (C):[(A) + (B)] = | | 0.15 g |

The preceding hair treatment is produced and applied in the manner described in Examples 11 to 18. Damaged hair has good combability and greater fullness (body effect) after the application of the hair treatment.

Example 20:
Production of pearlescent hair conditioning compositions

| Component I | | | |
|---|---|---|---|
| (A) | glycerin monolauric acid ester | | 10.00 g |
| (C) | stearyltrimethylammonium chloride | | 2.62 g |
| | dyestuff | | 1.00 g |
| | perfume oil | | 0.50 g |
| | water | | 85.88 g |
| | | | 100.00 g |

| Component II | | (a) | (b) |
|---|---|---|---|
| (B) | cetylstearyl alcohol | 4.0 g | 6.0 g |
| (C) | trimethylhexadecylammonium chloride | 1.0 g | 0.5 g |
| | perfume oil | 0.5 g | 0.5 g |
| | water | 94.5 g | 93.0 g |
| | | 100.0 g | 100.00 g |

Component I is mixed cold with component IIa or IIb in a ratio of 1 to 5. A stable, pearlescent hair conditioning composition with very good hair grooming properties is obtained.

In Examples 1 to 20 a commercial product was used as glycerin monolauric acid ester whose content of glycerin monolauric acid ester is at least 90 percent by weight.

The percentages in the present Application are percent b weight unless otherwise indicated.

While the invention has ben illustrated and described as embodied in a storage-stable pearlescent hair-conditioning composition, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

We claim:

1. Storage-stable, pearlescent hair conditioning composition consisting of:

(A) 0.2 to 10 percent by weight glycerin monolauric acid ester, (B) 0.2 to 10 percent by weight of a straight-chain fatty alcohol with 10 to 18 carbon atoms or a mixture of the fatty alcohols, (C) 0.050 to 5 percent by weight of a quaternary compound of the general formula (I):

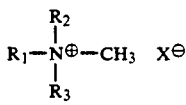

or a quaternary compound of the general formula (II):

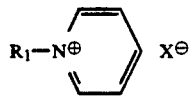

wherein $R_1$ is an alkyl radical having 12 to 22 carbon atoms, cocamidoethyl, cocamidopropyl or R'—Y—, and R' is an alkyl radical having 12 to 22 carbon atoms, and Y is —O—CO—CH$_2$— or —CO—O—CH$_2$—CH$_2$—; and wherein $R_2$ is CH$_3$, CH$_2$CH$_2$OH or CH$_2$CH$_3$, and wherein $R_3$ is CH$_3$, CH$_2$CH$_2$OH, benzyl or acetamidyl, and wherein X is Cl, Br, CH$_3$SO$_4$, ½ SO$_4$, dihydrogen phosphate, lactate or acetate; and (D) 70 to 99.595 water; and (E) 0 to 5 percent by weight of an additive selected from the group consisting of cosmetic dyestuffs, perfume oils, preservatives, vitamins, antioxidants, thickeners, cosmetic oils, cationic polymers and antidandruff ingredients;

wherein the additive is not present in a greater percentage by weight than the sum of the percentages by weight of the glycerin monolauric acid ester, the fatty alcohol and the quaternary compound, and wherein the percent by weight of the glycerin monolauric acid divided by the percent by weight of the fatty alcohol is from 0.3 to 5, and wherein the percent by weight of the quaternary compound divided by a sum of the percent by weight of the glycerin monolauric acid and the fatty alcohol is from 0.01 to 0.4.

2. Composition according to claim 1, wherein said glycerin monolauric acid is present in an amount of from 0.5 to 4 percent by weight.

3. Composition according to claim 1, wherein said fatty alcohol is selected from the group consisting of lauryl alcohol, tetradecanol, cetyl alcohol, stearyl alcohol and a 1:1 mixture of cetyl alcohol and stearyl alcohol.

4. Composition according to claim 1, wherein said fatty alcohol is present in an amount of from 0.8 to 5 percent by weight.

5. Composition according to claim 1, wherein said quaternary compound is selected from the group consisting of lauryl trimethylammonium chloride, tetradecyltrimethylammonium chloride, cetyltrimethylammonium chloride, stearyltrimethylammonium chloride, cetyldimethylbenzylammonium chloride, cetylpyridinium chloride, cetyldimethylhdroxyethylammonium dihydrophosphate, lauric acid choline ester chloride, betaine cetylester chloride and coconut fatty acid amidopropyldimethylacetamidylammonium chloride.

6. Composition according to claim 1, wherein said quaternary compound is contained in an amount of from 0.1 to 1.5 percent by weight.

7. Composition according to claim 1, wherein said water is contained in an amount of from 90 to 97 percent by weight.

8. A storage-stable, pearlescent hair conditioning composition consisting of:

(A) 0.2 to 10 percent by weight glycerin monolauric acid ester, (B) 0.2 to 10 percent by weight of a straight-chain fatty alcohol with 10 to 18 carbon atoms or a mixture of said fatty alcohols, (C) 0.050 to 5 percent by weight of a quaternary compound selected from the group consisting of compounds having the general formula (I):

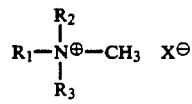

and compounds having the general formula (II):

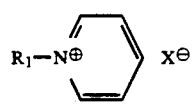

wherein $R_1$ is selected from the group consisting of alkyl radicals having 12 to 22 carbon atoms, cocamidoethyl, cocamidopropyl and R'—Y—, and R' is selected from the group consisting of alkyl radicals having 12 to 22 carbon atoms, and Y is selected from the group consisting of —O—CO—CH$_2$— and —CO—O—CH$_2$—CH$_2$—; and wherein $R_2$ is selected from the group consisting of CH$_3$, CH$_2$CH$_2$OH and CH$_2$CH$_3$, and wherein $R_3$ is selected from the group consisting of CH$_3$, CH$_2$CH$_2$OH, benzyl and acetamidyl, and wherein X is selected from the group consisting of Cl, Br, CH$_3$SO$_4$, ½ SO$_4$, dihydrogen phosphate, lactate and acetate; and (D) 70 to 99.595 water;

(E) 0 to 5 percent by weight of an additive selected from the group consisting of cosmetic dyestuffs, perfume oils, preservatives, vitamins, antioxidants, thickeners, cosmetic oils, cationic polymers and antidandruff ingredients; and (F) 1 to 10 percent by weight of a propellant, wherein said additive is not present in a greater percentage by weight than the sum of the percentages by weight of said glycerin monolauric acid ester, said fatty alcohol and said quaternary compound, and wherein said percent by weight of said glycerin monolauric acid divided by said percent by weight of said fatty alcohol is from 0.3 to 5, and wherein said percent by weight of said quaternary compound divided by a sum of said percent by weight of said glycerin monolauric acid and said fatty alcohol is from 0.01 to 0.4.

* * * * *